United States Patent [19]

van Duyn

[11] Patent Number: Plant 6,751

[45] Date of Patent: Apr. 25, 1989

[54] ALSTROEMERIA NAMED SUNNY WAY

[75] Inventor: Cornelis van Duyn, Rijnsburg, Netherlands

[73] Assignee: Groot Associates II, Irvine, Calif.

[21] Appl. No.: 57,234

[22] Filed: Jun. 1, 1987

[51] Int. Cl.[4] ..... A01H 5/00

[52] U.S. Cl. ..... Plt./68

[58] Field of Search ..... Plt./68

*Primary Examiner*—Robert E. Bagwill

*Attorney, Agent, or Firm*—Jackson & Jones

[57] ABSTRACT

A new Alstroemeria variety characterized by the distinctive reddish orange coloration of its blossoms, the inside petals of which are covered with longitudinal flecks or streaks of a darker shade of reddish orange and reddish orange with yellow dark striped hearts. The plant is early in flowering with relatively thick flower stems.

1 Drawing Sheet

BACKGROUND OF THE INVENTION

This new Alstroemeria originated as a seedling selected from individual members of breeding stock maintained at Rijnsburg, Holland. The particular seedling was selected by me in 1978 at Rijnsburg for propagation and testing because of the distinctive coloration of its blossoms produced on upright compact stems. Specifically, the inner petals are reddish orange with dark yellow striped hearts. The outer petals are solid in reddish orange coloring. The selected plant was propagated by me at Rijnsburg, Holland through several generations of root divisions to establish that its distinctive characteristics hold true from generation to generation and appear to be firmly fixed.

Breeding efforts commenced in 1974 and propagation is currently being carried out at Rijnsburg, Holland. This particular Alstroemeria, Sunny Way, does not resemble any other variety of Alstroemeria.

DESCRIPTION OF THE DRAWING

This new variety of the Alstroemeria plant is illustrated by the accompanying photograph which shows a blooming umbel of the plant with buds and flowers in various stages of opening.

DESCRIPTION OF THE NEW PLANT

The following is a detailed description of my new Alstroemeria plant with color designations according to The National Bureau of Standards, Standard Reference Material #2107, comprising the ISCC-NBS Centroid Color Charts and NBS Special Publication, #440.

THE PLANT

Origin: Seedling.
Parentage: Seed parent.
Classification: Alstroemeria hybrid.
Form: A generally erect bush having an upright stalk with flower-bearing branches in simple umbel arrangement at its top.
Height: About 1.65 meters.
Growth: Upright.
Root stock: Tuberous.
Foliage:
- *Quantity.*—Abundant.
- *Number of leaves.*—12 per stem.
- *Size of leaf.*—About 13.0 cm×2.6 cm.
- *Shape of leaf.*—Parallel venation.

- *Texture.*—Smooth.
- *Color.*—Upper side Light green. Under side Light green.

THE BUD

Form: Long pear shaped.
Size: Large.
- *Diameter.*—About 1.2 cm.
- *Length.*—About 3.5 cm.

Penduncle:
- *Length.*—About 15 cm.
- *Texture.*—Smooth.
- *Form.*—Erect.

THE FLOWER

Blooming habit: Profusely during early season in Fall.
Flower size: Medium.
- *Diameter.*—About 6.5 cm.
- *Depth.*—About 5.0 cm.

Borne: Terminal clusters.
Shape: Generally cup shaped.
Petalage:
- *Number of petals.*—Six.
- *Arrangement.*—Two concentric circles of three.
- *Form.*—Broad oval.
- *Texture.*—Soft.
- *Appearance.*—Velvety.

Color:
- *Outer Petals.*—Soft reddish orange (No. 35).
- *Inner petals.*—Moderate reddish orange (No. 36) with vivid yellow heart (No. 82). Inside petals have numerous generally longitudinal stripes or flecks of strong reddish brown (No. 44).

Persistance: The flowers hang and dry.
Main stem or stalk:
- *Length.*—About 15 cm.
- *Color.*—Green.
- *Character.*—Strong and upright.

Lasting quality of flower: About three weeks. As a cut flower, about 10–14 days.

REPRODUCTIVE ORGANS

Stamens:
- *Number.*—Six.
- *Arrangement.*—One opposite each petal.

Anthers:
- *Size.*—About 0.7 cm×0.2 cm.
- *Color.*—Dark grayish reddish brown (No. 47).

Filaments:

*Length.*—About 2.5 cm.

*Color.*—Moderate reddish orange (No. 36).

*Pollen.*—Yellow.

Pistils:

*Number.*—One.

*Styles.*—Length: About 2.5 cm to 3.0 cm. Color: Light red.

Fruit:

*Shape.*—Oblong.

*Color.*—Light brown.

This plant is particularly noted for the distinctive coloration of its flowers, which coloration does not clearly resemble that of any other Alstroemeria plant previously known to me. The moderate reddish orange petals along with the moderate reddish orange inner petals with dark yellow hearts and dark reddish orange flecks make this plant an attractive addition to the Alstroemeria family.

I claim:

1. A new and distinctive Alstroemeria cultivar, substantially as herein shown and described, characterized by the distinctive coloration of its medium sized and profusely blooming flowers.

* * * * *

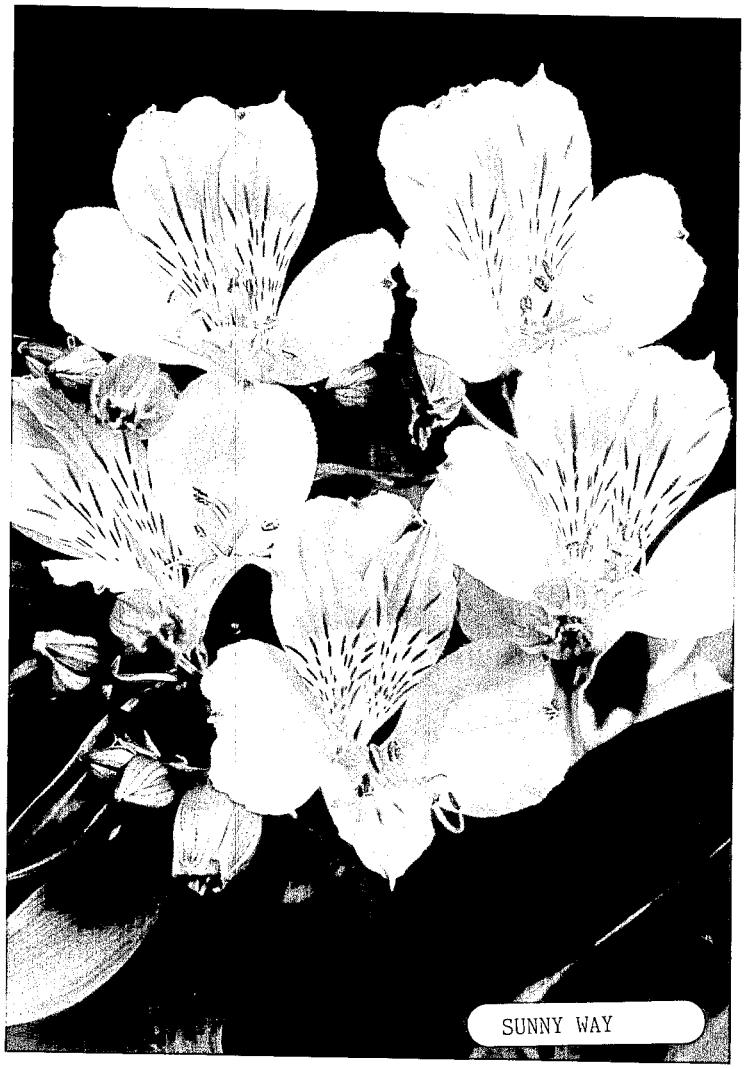

U.S. Patent Apr. 25, 1989 Plant 6,751